United States Patent
Kogan

(10) Patent No.: US 11,324,255 B1
(45) Date of Patent: May 10, 2022

(54) CONTAINER FOR DRY VAPORIZATION OF HERBS

(71) Applicant: Flor Brands, LLC, Salinas, CA (US)

(72) Inventor: Gavin Kogan, Carmel Valley, CA (US)

(73) Assignee: FLOR BRANDS LLC, Salinas, CA (US)

( * ) Notice: Subject to any disclaimer, the term of this patent is extended or adjusted under 35 U.S.C. 154(b) by 328 days.

(21) Appl. No.: 16/660,690

(22) Filed: Oct. 22, 2019

Related U.S. Application Data

(60) Provisional application No. 62/749,606, filed on Oct. 23, 2018.

(51) Int. Cl.
   *A24F 40/42* (2020.01)
   *A24F 40/20* (2020.01)
   *A61M 11/04* (2006.01)

(52) U.S. Cl.
   CPC .............. *A24F 40/42* (2020.01); *A24F 40/20* (2020.01); *A61M 11/041* (2013.01); *A61M 2205/3368* (2013.01)

(58) Field of Classification Search
   None
   See application file for complete search history.

(56) References Cited

U.S. PATENT DOCUMENTS

| | | | |
|---|---|---|---|
| 2017/0119048 A1* | 5/2017 | Kaufman | A24D 1/20 |
| 2017/0157106 A1* | 6/2017 | Rogers | A24D 1/025 |
| 2018/0084831 A1* | 3/2018 | Mironov | A24F 40/42 |
| 2021/0169139 A1* | 6/2021 | Mercer | A24F 23/02 |

* cited by examiner

*Primary Examiner* — James Harvey
(74) *Attorney, Agent, or Firm* — Patrick Bright

(57) ABSTRACT

In one embodiment, a sachet configured to contain an herbal substance, the sachet including a natural fiber layer of a first thickness that is configured to combust at a first temperature, wherein the natural fiber layer is shaped to receive the herbal substance, wherein the herbal substance is configured to vaporize at a second temperature that is less than the first temperature, and a heat tolerant sealant configured to seal the natural fiber layer to contain the herbal substance, wherein the heat tolerant sealant is configured to deteriorate at a third temperature that is greater than the first temperature.

14 Claims, 5 Drawing Sheets

CONTAINER FOR DRY VAPORIZATION OF HERBS

PRIORITY

This application claims the benefit under 35 U.S.C. § 119(e) of U.S. Provisional Patent Application No. 62/749,606, filed 23 Oct. 2018, which is incorporated herein by reference.

TECHNICAL FIELD

This disclosure generally relates to containers for herbal substances, and in particular relates to a sachet for containing herb substances for use in a dry vaporizer.

BACKGROUND

The beneficial value of cannabis has been discovered in more recent years. More benefits are discovered with various methods of consumption of cannabis. A user may smoke cannabis to gain benefits ranging from achieving a relaxed state to achieving a more focused state. While the benefits are being explored by users, methods of consuming cannabis are being explored as well. These different methods of consumption provide different advantages and disadvantages. A popular method of consumption includes combusting cannabis (e.g., smoking from a joint or pipe) to inhale the chemicals released from the cannabis. However, there are several by-products with the combusting method, namely carbon monoxide. Another popular method of consumption may be vaporizing oils that are extracted from the cannabis plant, which may be consumed either through inhalation or imbibing products that contain the oils. However, harsh chemicals are associated with the process to extract the oils from cannabis. Additionally, the extracted oils may make up only a certain percentage of the actual chemicals found in the original cannabis. For instance, the extraction process may be to extract the tetrahydrocannabinol (THC) from cannabis. However, other chemicals such as the cannabidiol (CBD) may be lost during the extraction process. Additionally, the terpenes from the cannabis plant (which have flavors and benefits themselves) may be removed during the extraction process. Therefore, the use of these oils may not result in the same benefits as consuming the original cannabis. As a result, other methods of consumption may be used to provide the same benefits of cannabis without the by-products associated with the method. For example, vaporizing cannabis is a method that releases the chemicals of cannabis without the harmful by-products of combusting.

SUMMARY OF PARTICULAR EMBODIMENTS

In particular embodiments, the sachet may be configured to contain an herbal substance, such as cannabis. The sachet may be used in a vaporizer device to vaporize the herbal substance without combusting the herbal substance. A heating element within the vaporizer device may be used to produce heat for a vaporization process. In particular embodiments, the vaporization process may comprise heating the herbal substance within a threshold range of temperatures for a time period to vaporize the herbal substance without combusting the herbal substance. In particular embodiments, a fan may be used to transfer heat within the vaporizer device or the airflow may be provided from inhalation of a user of the vaporizer device. One of the advantages of vaporizing the herbal substance may be the chemicals from the herbal substance are released while avoiding the by-products of combusting the herbal substance (i.e., carbon monoxide, etc.). In particular embodiments, the herbal substance may include cannabis, tobacco, sage, chamomile, lavender, and the like. The herbal substance may be a combination of one or more strains of cannabis, tobacco, and the like. As an example and not by way of limitation, the combination may comprise a portion of an indica-dominant strain of cannabis and another portion of a *sativa*-dominant strain. Alternatively, in another example and not by way of limitation, the combination may comprise mainly an indica-dominant strain of cannabis. The combination may be configured to achieve a particular effect. In particular embodiments, the combination may yield a release of specific threshold levels of chemicals associated with the herbal substance during a vaporization process. As an example and not by way of limitation, the vaporization process may release a threshold level of tetrahydrocannabinol (THC) and a threshold level of cannabidiol (CBD). As another example and not by way of limitation, the vaporization process may release a threshold level of terpenes. The terpenes may be important to the effects of vaporizing a cannabis plant. Although this disclosure may refer to THC and CBD as a particular chemical by-product of a vaporization process, other cannabinoids may be discussed as chemical by-products of the vaporization process.

The embodiments disclosed herein are only examples, and the scope of this disclosure is not limited to them. Particular embodiments may include all, some, or none of the components, elements, features, functions, operations, or steps of the embodiments disclosed herein. Embodiments according to the invention are in particular disclosed in the attached claims directed to a method, a device, or product, wherein any feature mentioned in one claim category, e.g. method, can be claimed in another claim category, e.g. device, as well. The dependencies or references back in the attached claims are chosen for formal reasons only. However, any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed comprises not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

DESCRIPTION OF EXAMPLE EMBODIMENTS

Sachet Overview

Figure 1A:
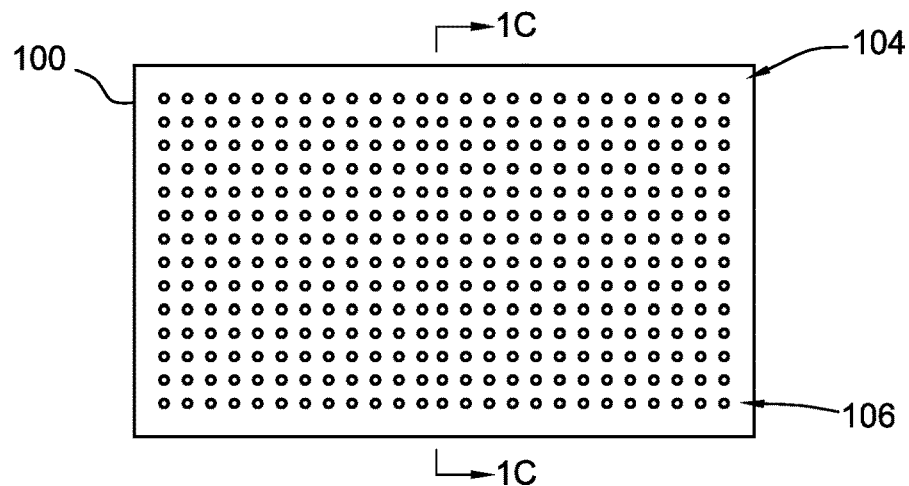
FIGS. 1A-1C illustrate different perspective views of a sachet containing an herbal substance.

FIG. 1A illustrates a top perspective view of an example sachet 100 configured to contain an herbal substance 102. The sachet 100 may be used in a vaporizer device to vaporize the herbal substance 102 without combusting the herbal substance 102. A heating element within the vaporizer device may be used to produce heat for a vaporization process. In particular embodiments, the vaporization process may comprise heating the herbal substance 102 within a threshold range of temperatures for a time period to vaporize the herbal substance 102 without combusting the herbal substance 102. As an example and not by way of limitation, the time period may be approximately 10-15 seconds, though shorter and longer periods are possible. The time period may comprise several phases, such as a warming phase, a heating phase, and an inhalation phase. In particular embodiments, a fan may be used to transfer heat within the vaporizer device or the airflow may be provided from inhalation of a user of the vaporizer device. One of the advantages of vaporizing the herbal substance 102 may be the chemicals from the herbal substance 102 are released while avoiding the by-products of combusting the herbal substance 102 (i.e., carbon monoxide, etc.). In particular embodiments, the herbal substance 102 may include cannabis, tobacco, and the like. The herbal substance 102 may be a combination of one or more strains of cannabis, tobacco, and the like. As an example and not by way of limitation, the combination may comprise a portion of an indica-dominant strain of cannabis and another portion of a sativa-dominant strain. Alternatively, in another example and not by way of limitation, the combination may comprise mainly an indica-dominant strain of cannabis. The combination may be configured to achieve a particular effect. In particular embodiments, the combination may yield a release of specific threshold levels of chemicals associated with the herbal substance 102 during a vaporization process. As an example and not by way of limitation, the vaporization process may release a threshold level of tetrahydrocannabinol (THC) and a threshold level of cannabidiol (CBD). As another example and not by way of limitation, the vaporization process may release a threshold level of terpenes. The terpenes may be important to the effects of vaporizing a cannabis plant. Although this disclosure may refer to THC and CBD as a particular chemical by-product of a vaporization process, other cannabinoids may be discussed as chemical by-products of the vaporization process.

In particular embodiments, the sachet 100 may comprise a bag material 104. As an example and not by way of limitation, the sachet 100 may be made of a paper product, hemp, or other bag material 104 with a high level of thermal conductivity. The high level of thermal conductivity may allow for the sachet 100 to transfer heat from a heating element to the herbal substance 102 contained within the sachet 100. In particular embodiments, the bag material 104 may comprise a material that retards heat transfer from a heating element to the herbal substance 102 (e.g., an insulating material with a relatively low thermal conductivity). In particular embodiments, the bag material 104 may comprise a plurality of layers. The outer layer may comprise a material that insulates the inner layer from a heating element. In particular embodiments, the sachet 100 may comprise a threshold thickness to maintain structural integrity at high temperatures while having a high level of thermal conductivity. For instance, a high thickness may yield a higher heat resistance. Alternatively, a smaller thickness may result in a lower heat resistance for the same material. The thickness of the sachet 100 may also affect the temperature at which the herbal substance 102 is vaporized. This may be the result of the heat transfer from a heating element to the sachet 100 being reduced with a higher thickness and vice versa. In particular embodiments, the mass of the material may be threshold amount of mass per a given surface area. As an example and not by way of limitation, the range of mass per surface area may be from 16.5 g/m$^2$ to 38 g/m$^2$. In particular embodiments, the mass of the bag material 104 may be greater than the mass of the herbal substance 102. In particular embodiments, the bag material 104 of the sachet 100 may be selected to have a higher threshold combusting temperature than the herbal substance 102. In particular embodiments, the sachet 100 may release natural by-products during the vaporization process. In particular embodiments, if the sachet 100 contains a cellulose layer, the pyrolysis products of the cellulose layer may comprise one or more of water vapor, carbon monoxide, carbon dioxide, levoglucosan, hydroxyzcetaldehyde, hydroxyacetone, pyruvic aldehyde, glyceraldehyde, hydroxymethyl-furfural and furfural, along with aliphatic oxygenated C2-4 organic compounds. Another advantage of vaporizing the herbal substance 102 may be the temperatures utilized to vaporize the herbal substance 102 allows for the sachet 100 to remain intact after the vaporization process. As an example and not by way of limitation, the sachet 100 may maintain its shape and structural integrity after the vaporization process. In particular embodiments, the temperatures associated with the vaporization process may range from 350 degrees Fahrenheit to 420 degrees Fahrenheit. Although a specific range is mentioned, the range for the vaporization process may be any temperature range to vaporize a particular herbal substance 102 without combusting the herbal substance 102 and/or combusting a container of the herbal substance 102. In particular embodiments, the sachet 100 may comprise hydrophobic properties to allow for the transfer of vapor (e.g., from the vaporization of the herbal substance 102) from inside the sachet 100 to be released out of the sachet 100. In particular embodiments, the sachet 100 may comprise a threshold level of permeability to allow for the transfer of vapor from inside the sachet 100 to be released out of the sachet 100. In particular embodiments, the sachet 100 may comprise at least two layers, where the interior layer may be hydrophilic to maintain product moisture and the exterior layer may be hydrophobic. The sachet 100 may comprise high-quality fibers to maintain structural integrity through one or more vaporization processes. As an example and not by way of limitation, the sachet 100 may be built of a bag material 104 to withstand six vaporization processes (e.g., temperatures of up to 420 degrees Fahrenheit for 3 seconds) without compromising the structural integrity of the sachet 100 (e.g., maintain the sachet's 100 form, reduce charring of the sachet 100, and contain a vaporized herbal substance 102). In particular embodiments, the bag material 104 of the sachet 100 may be selected to avoid emissions of volatile organic compounds (VOCs). In particular embodiments, the bag material 104 of the sachet 100 may comprise a plurality of layers, wherein at least two of the layers are different materials. As an example and not by way of limitation, the sachet 100 may comprise two cellulose layers and a thermoplastic layer to seal the two cellulose layers together. In particular embodiments, the thermoplastic layer may be exposed to appropriate temperatures to provide a seal. As an example and not by way of example, the thermoplastic layer may be exposed to temperatures to melt the thermoplastic layer to provide a seal between two separate cellulose layers. In particular embodiments, the bag material 104 of the sachet 100 may comprise two cellulose layers coupled to their own separate thermoplastic layers which become coupled together when exposed to high temperatures to form a seal between the two cellulose layers. As an example and not by way of limitation, the melting of the thermoplastic layers may form a hydroentanglement of the layers. In particular embodiments, the layers of the bag material 104 may be folded to prevent one layer (e.g., the thermoplastic layer) from contacting the herbal substance 102 and outside of the sachet 100. In particular embodiments, the bag material 104 may comprise any combination of different layers to contain the herbal substance 102. In particular embodiments, the bag material 104 may comprise a threshold level of porosity. A higher porosity may allow for greater heat transfer from a heating element to the herbal substance 102. A lower porosity may prevent heat transfer from a heating element to the herbal substance 102. In particular embodiments, the bag material 104 may be selected to have a threshold level of porosity to allow for a threshold level of heat transfer. In particular embodiments, a layer of the bag material 104 may comprise one or more of polyester, polypropylene, polyethylene, or any other kind of thermoplastic. The material of the layer of the bag material 104 may have a threshold melting point. In particular embodiments, the bag material 104 may comprise of a cellulose layer infused with a thermoplastic layer. In particular embodiments, the bag material 104 may comprise a material that releases negligible odor when exposed to a threshold temperature. In particular embodiments, the thermoplastic layer may have a range of melting points based on the material of the thermoplastic layer. While some thermoplastics may be ideal for use of the heat sealant layer, certain considerations are needed for selecting an appropriate thermoplastic for the thermoplastic layer. In particular embodiments, features of the thermoplastic used to select a suitable thermoplastic layer comprises one or more of melting point of the thermoplastic, the pyrolysis products of the thermoplastic, a glass transition temperature (if applicable), the temperature the thermoplastic decomposes, and other properties of the thermoplastic. As an example and not by way of limitation, the heating of particular thermoplastics may release dangerous chemicals, which the user would not want to inhale. As an example and not by way of limitation, several pyrolysis products that may be released by the thermoplastic layer may be one or more of carbon monoxide, carbon dioxide, and other hydrocarbons. In particular embodiments, the thermoplastic may not release pyrolysis products until a threshold temperature is reached. This threshold temperature may be significantly higher than the temperatures used in the vaporization process. In particular embodiments, certain thermoplastics react differently to being exposed to high temperatures. As an example and not by way of limitation, a thermoplastic may form a seal when temperatures drop slightly below the melting point, while other thermoplastics may require some time before a seal is formed. This may be beneficial for high-speed manufacturing purposes if the thermoplastic is able to form a seal quickly. In particular embodiments, a thermoplastic layer may be selected based on a determination that the selected thermoplastic will aid in maintaining structural integrity of the sachet 100 during the vaporization process. As an example and not by way of limitation, the thermoplastic layer may hold the sachet 100 together during the vaporization process. A thermoplastic may be selected for the thermoplastic layer even if it melts during the vaporization process so long as it does not compromise the structural integrity of the sachet 100 during the vaporization process. As an example and not by way of limitation, the thermoplastic layer may fuse again after the vaporization process to maintain the seal between the layers of the sachet 100.

In particular embodiments, the sachet 100 may comprise a plurality of perforations 106 as shown in FIG. 1A. These perforations 106 may be optional for the sachet 100. While FIG. 1A illustrates the sachet 100 with perforations 106, the sachet 100 may not have the perforations 106. These perforations 106 may allow airflow through the sachet 100 to improve the vaporization process. The perforations 106 may improve the thermal conductivity of the bag material 104 by allowing heat transfer through the sachet 100. In particular embodiments, the thickness of the bag material 104 of the sachet 100 may be increased to improve structural integrity of the substance while maintaining a high level of thermal conductivity by using the perforations 106. The thickness of the bag material 104 may be selected to provide structural integrity of the sachet 100 after a threshold number of vaporization processes. In particular embodiments, the sachet 100 may comprise a threshold number of perforations 106. The number of perforations 106 may be selected to achieve a threshold level of open space for the outer layer of the sachet 100. As an example and not by way of limitation, a certain amount of perforations 106 may be selected to achieve 80 percent open space for the outer layer of the sachet 100. In particular embodiments, the shape and/or size of the perforations 106 may be selected to provide airflow through the sachet 100 while containing the herbal substance 102 within the sachet 100. In particular embodiments, the size of the sachet 100 may be selected to contain a threshold amount of herbal substance 102. The threshold number of herbal substance 102 may be determined based on the amount of chemicals released from the vaporization process. As an example and not by way of limitation, the amount may be 1 gram of an herbal substance 102 to achieve a release of an expected amount of chemicals from the herbal substance 102 during the vaporization process. In particular embodiments, the size of the sachet 100 may be determined to allow for a threshold level of interstitial space between the particles of the herbal substance 102. As an example and not by way of limitation, if the herbal substance 102 comprises pieces of ground up flower, then the threshold level of interstitial space may be 10 micrometers between the pieces of ground up flower. A threshold level of interstitial space may be required to allow airflow through the herbal substance 102 within the sachet 100. If there is not enough interstitial space within the herbal substance 102, the herbal substance 102 may not vaporize evenly and/or heat may not be transferred effectively throughout the herbal substance 102. In particular embodiments, the size of the sachet 100 may be selected to minimalize the bag material 104 to herbal substance 102 ratio. Thereby the amount of herbal substance 102 may be maximized for the amount of bag material 104. In particular embodiments, the size of the sachet 100 may be selected based on the dimensions of a standard of a vaporizer device. As an example and not by way of limitation, the sachet 100 may comprise dimensions to fit within an oven that measures ⅞ inch×⅜ inch×⅜ inch. In particular embodiments, the size of the sachet 100 and the amount of herbal substance 102 may be selected in combination to provide enough excess space within the sachet 100. In particular embodiments, the size and shape of the sachet 100 may be selected to be a customized to fit a particular dimension. As an example and not by way of limitation, a particular brand of a vaporizer device may have specific dimensions that sachet 100 may be made to create a perfect fit where the sachet 100 is flush with the inside of the oven receptacle. In particular embodiments, the size and shape of the sachet 100 may be selected to be a universal/standardized fit to generally fit into a wide variety of vaporizer devices on the market. As an example and not by way of limitation, the size and shape of the sachet 100 may be selected to fit into at least the smallest popular vaporizer devices on the market. As another example and not by way of limitation, the size and shape of the sachet 100 may conform to industry-standardized dimensions to fit into devices that follow the same industry standards. In particular embodiments, the sachet 100 may be malleable, such that it can be manipulated to fit into a variety of oven shapes.

Figure 1B:
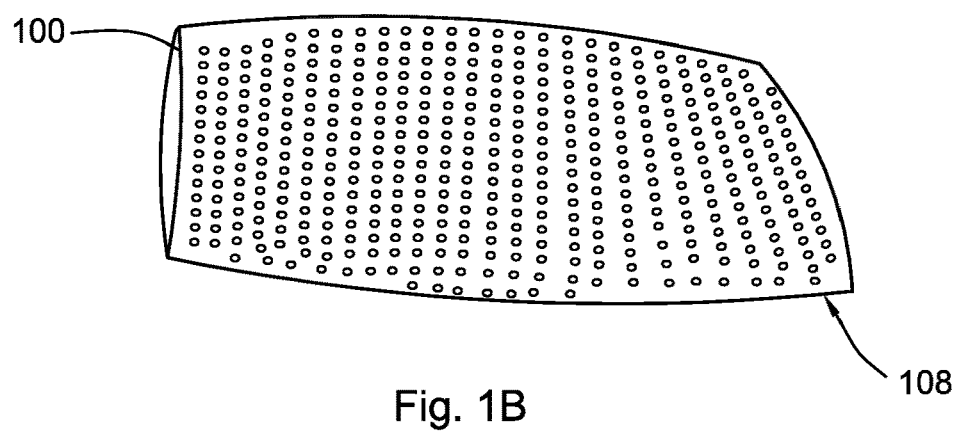

Referring to FIG. 1B, the sachet 100 is shown in a side perspective view. In particular embodiments, the sachet 100 may be generally shaped as a pouch containing an herbal substance 102. Although, in particular embodiments, the sachet 100 may be shaped in any way to effectively contain an herbal substance 102. As an example and not by way of limitation, the sachet 100 may be shaped as a cuboid, a sphere, and other shapes to contain the herbal substance 102. In particular embodiments, the sachet 100 may be shaped as a square packet. In particular embodiments, there may be a standard size for a vaporizing oven to receive the sachet 100. In particular embodiments, the sachet 100 may be shaped in such a way to fit the standard size of the oven (e.g., rectangular, trapezoidal, oblong, circular). In particular embodiments, the sachet 100 may be sealed to contain an herbal substance 102. As an example and not by way of limitation, the sachet 100 may comprise two layers of a bag material 104 that is sealed together on all sides of the sachet 100 to contain the herbal substance 102 inside. In particular embodiments, one layer of a bag material 104 may be folded over (e.g., like folding a paper in half) to contain the herbal substance 102 and sealed on three sides of the sachet 100. In particular embodiments, the sides of the sachet 100 may be stitched by a natural material 108 to seal the sides of the sachet 100. In particular embodiments, the sides of the sachet 100 may be heat sealed. In particular embodiments, the sachet 100 may be folded to seal the sides of the sachet 100 to contain an herbal substance 102. In particular embodiments, the sachet 100 may comprise a tab or an extension that allows for the sachet 100 to be handled without touching the sachet 100. As an example and not by way of limitation, the sachet 100 may have a foldable tab that extends out without any force applied. As another example and not by way of limitation, the sachet 100 may comprise a string that may be pulled to handle the sachet 100. The tab or string may allow for a user to handle the sachet 100 without touching the heating element or hot surfaces.

Figure 1C:
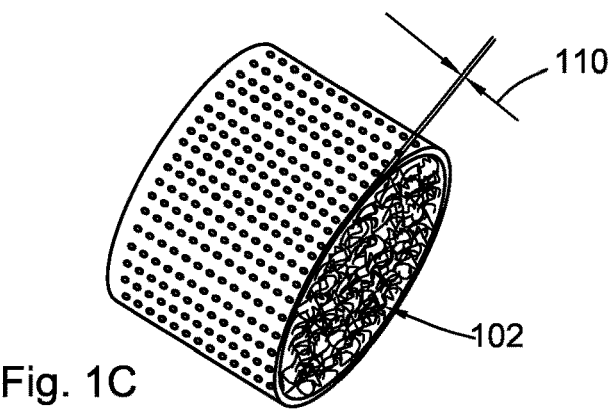

FIG. 1C illustrates a cross-sectional view of FIG. 1A where the herbal substance 102 is shown inside the sachet 100. The bag material 104 of the sachet 100 may have a threshold thickness 110. In particular embodiments, the herbal substance 102 may be ground up to a threshold level. As an example and not by way of limitation, the herbal substance 102 may be ground up to several clusters of the herbal substance 102. The herbal substance 102 may be ground up to achieve a threshold level of interstitial space as described above. A combination of various factors may determine the threshold level of how to grind the herbal substance 102. In particular embodiments, the interstitial space, the size of the sachet 100, the perforations 106, the thermal conductivity of the bag material 104, the herbal substance 102, and the vaporization process (e.g., temperatures used and duration of the process) may determine the threshold level of how to grind the herbal substance 102. As an example and not by way of limitation, for a sachet 100 that contains a tightly packed amount of herbal substance 102 (i.e., a very low level of interstitial space within the herbal substance 102), the herbal substance 102 may be ground up to a finer level. In particular embodiments, the finer the ground of the herbal substance 102 may yield a higher heat transfer from a heating element to the herbal substance 102. The higher heat transfer may result from airflow passing through the small particles of the herbal substance 102. As another example and not by way of limitation, if the sachet 100 comprises perforations 106 that make up 80 percent of the outer layer, then the herbal substance 102 may be ground up to a coarser level to prevent the herbal substance 102 from leaking from the sachet 100. In this case, the coarser level may provide a higher level of interstitial space within the herbal substance 102. In particular embodiments, the grinding of the herbal substances 102 may remove some of the desired properties of the herbal substance 102 and so a coarser grind may be desired. As an example and not by way of limitation, the herbal substance 102 may be cannabis and grinding the cannabis may remove the cannabinoids from the cannabis. To prevent an excessive amount of cannabinoid loss from grinding, a coarser ground of cannabis may be desired. However, the coarser ground may require more heat as compared to a finer grind of the herbal substance 102. As such, the perforations 106 may allow for better heat transfer to a coarser grind of an herbal substance 102 and improves the thermal conductivity of the sachet 100 by allowing more airflow through the sachet 100. In particular embodiments, the sachet 100 reduces the cannabinoid loss of excessive grinding by implementation of the perforations 106 to improve airflow within the sachet 100. In particular embodiments, the size of the sachet 100 may allow for a coarser grind of the herbal substance 102 by providing more interstitial space within the herbal substance 102. As shown in FIG. 1C, the grind level of the herbal substance 102 allows for the herbal substance 102 to be contained within the sachet 100 even though the sachet 100 contains the perforations 106. In particular embodiments, the interstitial space within the sachet 100 may be enough to allow for the sachet 100 to change shapes to conform to a receptacle that receives the sachet 100. As an example and not by way of limitation, sachet 100 may initially shaped as a cuboid, but when inserted into a receptacle, the sachet 100 may conform to the spherical shape of the receptacle.

Manufacturing Overview

In particular embodiments, the sachet 100 may be manufactured in an industrial setting. In particular embodiments, a device may manufacture the sachet 100. The manufacturing process may include equipping the manufacturing device with the bag material 104. In particular embodiments, the manufacturing device may shape the bag material 104 into the general shape of the sachet 100. As an example and not by way of limitation, the manufacturing device may fold the bag material 104 into a cylinder. As another example and not by way of limitation, the bag material 104 may be shaped into a U-shape. As another example and not by way of limitation, the bag material 104 may be shaped into a V-shape. In particular embodiments, the manufacturing device may use a roll of bag material 104 to generate the sachet 100. As an example and not by way of limitation, the roll of bag material 104 may be 1 inch wide and the roll of bag material 104 may be at least 12 inches in diameter. In particular embodiments, the manufacturing process may determine the size of the sachet 100. As an example and not by way of limitation, if a roll of bag material 104 is fed into a manufacturing device to be shaped in a V-shape manner, the sachet 100 may result in a smaller size than if a sachet 100 were generated with two layers of bag material 104 sealed together. In particular embodiments, the manufacturing process may be selected based on the desired size of the sachet 100. In particular embodiments, the manufacturing device may generate perforations 106 by inserting a plurality of tiny pins into the bag material 104. The manufacturing device may use a specific equipment to generate customized perforations 106. The manufacturing device may be able to quickly fill the bag material 104 with the herbal substance 102 through insertion of the herbal substance 102 into the shaped bag material 104 (e.g., into a cylinder or into a U-shaped cradle). In particular embodiments, the manufacturing device may create sections of the bag material 104 indicative of a single sachet 100. In particular embodiments, the manufacturing device may separate each of the sections to create a plurality of sachets 100. As an example and not by way of limitation, the manufacturing device may be configured to fill a certain amount of herbal substance 102 (e.g., 0.5 grams) into a roll of bag material 104 before sectioning off a sachet 100. As another example and not by way of limitation, the manufacturing device may be configured to layer a certain amount of herbal substance 102 onto the bag material 104. The manufacturing device may fill a certain amount of herbal substance 102 and section off the bag material 104 in such a way to allow for a threshold amount of interstitial space. As an example and not by way of limitation, a person may be able to conform the shape of the sachet 100 to a receptacle of varying shapes. In particular embodiments, the manufacturing device may insert another layer on the bag material 104 to form a seal. As an example and not by way of limitation, the manufacturing device may deposit a layer of thermoplastic fibers on top of the bag material 104 to be melted to provide a seal. In particular embodiments, the manufacturing device may section off the sachets 100 by one or more of using a heat element, stitching one or more sides of the sachets 100, or folding one or more sides of the sachets 100. As an example and not by way of limitation, the manufacturing device may use a sharp surface to separate each sachet 100 from one another. In particular embodiments, the manufacturing device may group a specific number of sachets together to be contained together. As an example and not by way of limitation, the manufacturing device may group five sachets 100 together. In particular embodiments, the manufacturing device may pack a group of sachets 100 together in a container.

In particular embodiments, the bag material 104 may comprise of natural fibers. The bag material 104 may be generated in large amounts to supply the manufacturing device to create a plurality of sachets 100. As an example and not by way of limitation, the bag material 104 may be generated in a shape of a roll that feeds into the manufacturing device. In particular embodiments, the manufacturing device may be configured to receive the bag material 104 to generate a plurality of sachets 100.

In particular embodiments, the manufacturing device may be configured to receive the herbal substance 102 to combine with the bag material 104 to create the sachets 100. The manufacturing device may be configured to receive a threshold amount of herbal substance to generate a proportional number of sachets 100 given a certain amount of bag material 104 the manufacturing device holds. The manufacturing device may receive the herbal substance 102 in a first state and grind the herbal substance 102 into a second state to combine with the bag material 104 to create the sachets 100. As an example and not by way of limitation, the manufacturing device may be filled with flowers of cannabis and the manufacturing device may grind the flowers to a grind level to insert into the sachets 100. Alternatively, as another example and not by way of limitation, the manufacturing device may receive pre-ground cannabis.

In particular embodiments, there may be multiple manufacturing devices each configured to perform one aspect of the manufacturing process. As an example and not by way of limitation, there may be on manufacturing device to generate the sachet 100 while another manufacturing device fills the sachet 100 with herbal substance 102.

Devices Configured to Receive Sachets Overview

In particular embodiments, vaporizer devices to receive the sachets may be developed with different configurations. The vaporizer devices may have a different receptacle size or oven size to receive a sachet 100. Each vaporizer device may have a different heating element and other mechanisms for heat transfer (e.g., whether it has a fan, or it uses inhalation from a user). Current utilization of vaporizer devices requires users to input an herbal substance into an oven chamber and vaporize the substance and subsequently remove the vaporized herbal substance. This process may cause a mess because of the individual pieces of vaporized substance that may progressively affect the oven chamber (e.g., leave remnants or residue within the oven chamber).

Utilizing Sachet within Devices

Figure 2A:
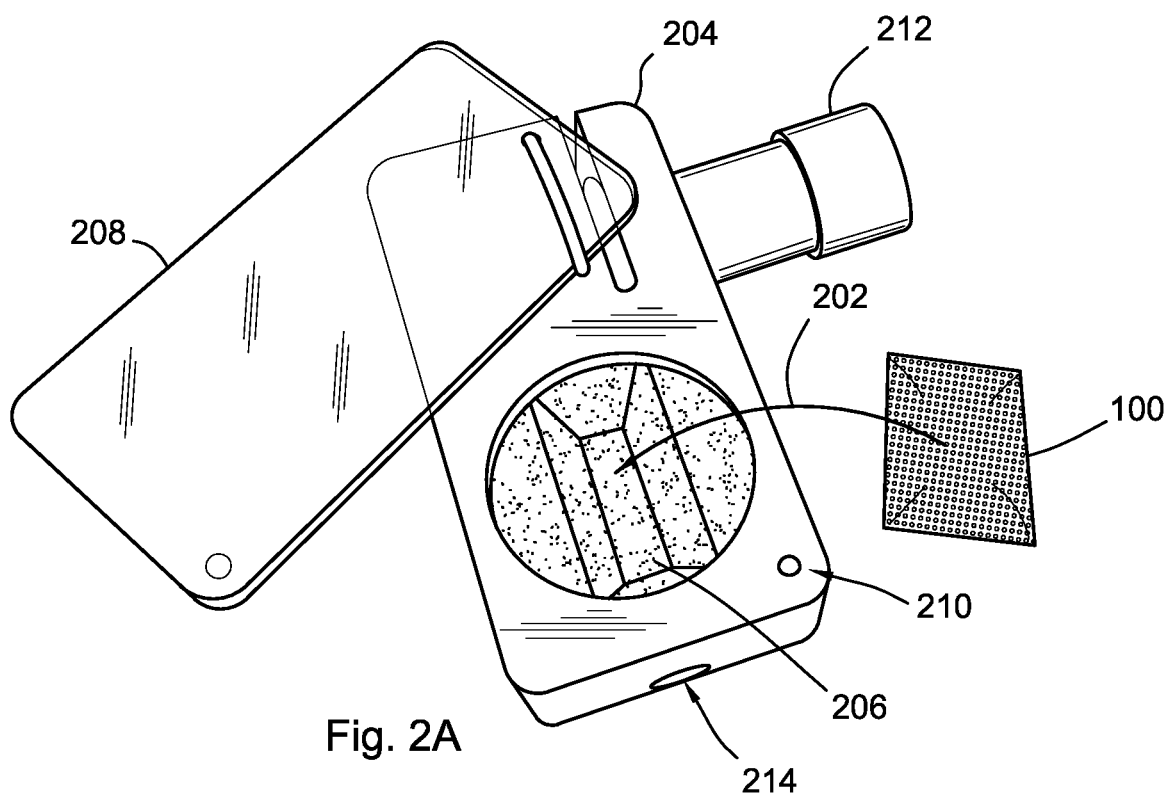
FIGS. 2A-2B illustrate an example process of utilizing a sachet within a vaporizer device.
Figure 2B:
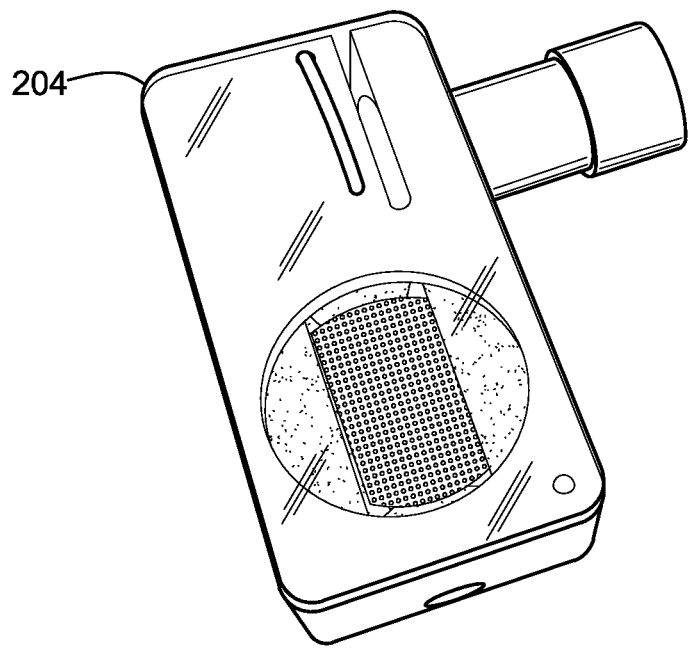

FIGS. 2A-2B illustrate an example process of utilizing a sachet 100 within a vaporizer device 204. Referring to FIG. 2A, a user may insert the sachet 100 along the path 202 into an oven chamber 206 of the vaporizer device 204. In particular embodiments, the sachet 100 may conform to the shape of the oven chamber 206 as shown in FIG. 2B. That is, the sachet 100 may have an original shape, but as a user inserts the sachet 100 into the oven chamber 206, the sachet 100 may be molded to fit the shape of the oven chamber 206. Referring back to FIG. 2A, the vaporizer device 204 may comprise a shield 208 to hold the sachet 100 within the oven chamber 206. In particular embodiments, the shield 208 may interface a locking mechanism 210 that retains the shield 208 in a locked position. The vaporizer device 204 may comprise a heating element battery 212 that may interface a heating element (not shown) to emit heat to vaporize an herbal substance 102 contained within the sachet 100. In particular embodiments, the heating element may emit temperatures that range from 350 to 420 degrees Fahrenheit. In particular embodiments, the vaporizer device 204 may comprise an inhalation hole 214. In particular embodiments, a user may inhale through the inhalation hole 214. In particular embodiments, the user may input an inhalation device (not shown) through the inhalation hole 214 to inhale vaporized herbal substance 102. As an example and not by way of limitation, a user may input a high temperature resistant straw into the inhalation hole 214. The vaporizer device 204 may rely upon the inhalation of the user to provide airflow to transfer heat through the herbal substance 102 within the sachet 100. The benefits of using the sachet 100 may be the sachet 100 contains the vaporized herbal substance 102 after the herbal substance has been vaporized. This may reduce the mess associated with loose herbal substance 102 that may be vaporized within the chamber 206. As described above, the sachet 100 may comprise a tab that may be folded down when the sachet 100 is inserted into the oven chamber 206. In particular embodiments, the tab may extend out of the oven chamber 206 subsequent to the user opening the shield 208 to expose the oven chamber 206. The user may pull the tab to extract the sachet 100, thereby allowing the user to safely and easily extract the sachet 100 without touching any potential hot surfaces. In another example and not by way of limitation, the sachet 100 may comprise a string. The user may pull on the string of the sachet 100 to handle the sachet 100 and extract the sachet 100 from the oven chamber 206. In particular embodiments, the sachet 100 may have any suitable kind of interface to allow a user to extract the sachet 100 without touching the oven chamber 206.

Figure 3A:
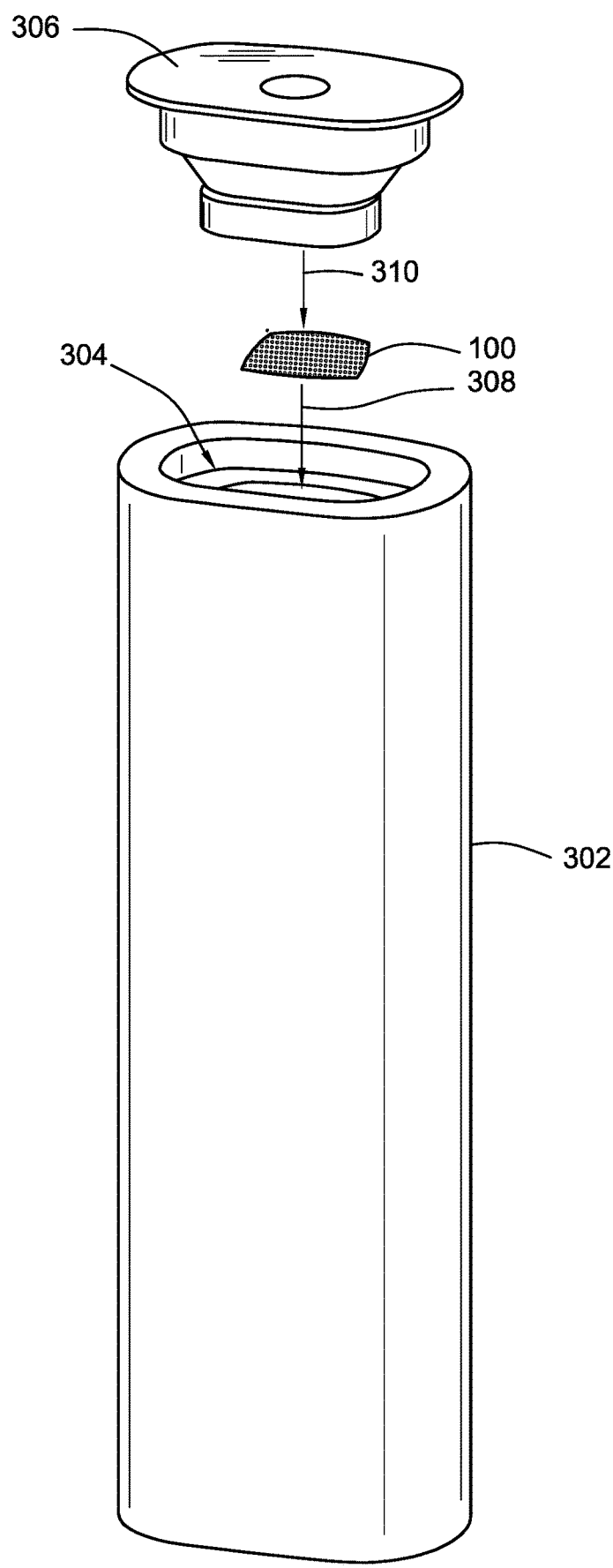
FIGS. 3A-3C illustrate another example process of utilizing a sachet within another vaporizer device.
Figure 3C:
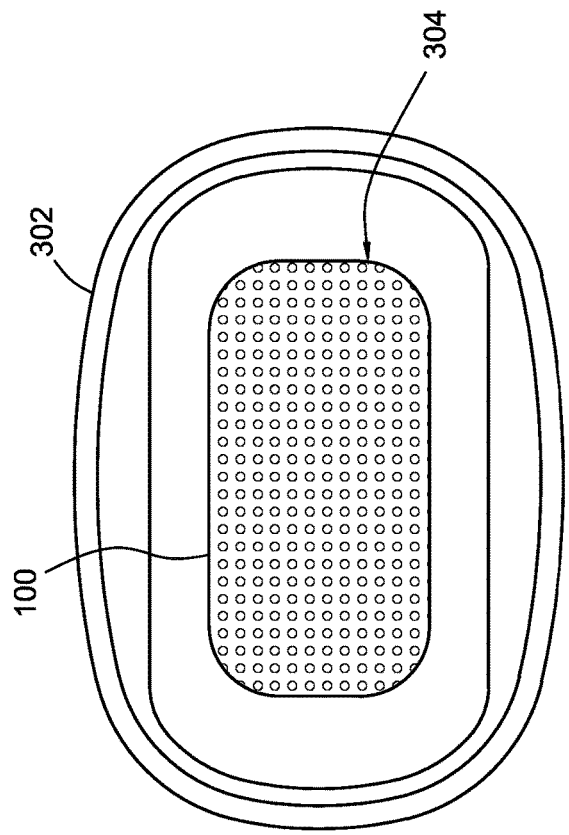
Figure 3B:
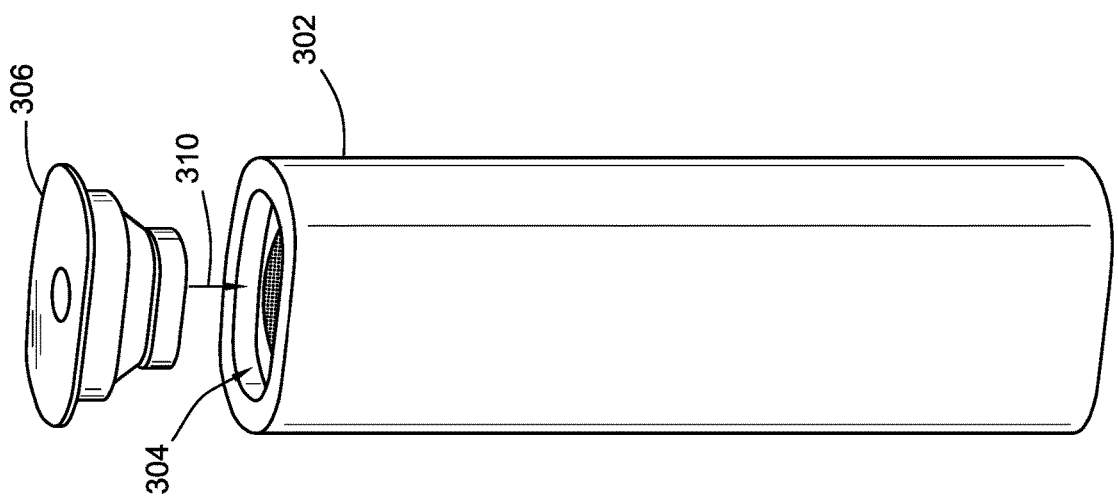

FIGS. 3A-3C illustrate another example process of utilizing a sachet 100 within another vaporizer device 302. Referring to FIG. 3A, a user may insert the sachet 100 within an oven chamber 204 of the vaporizer device 302. In particular embodiments, the vaporizer device 302 may comprise a top 306 to seal the oven chamber 304. The user inserts the sachet 100 following path 308 into the oven chamber 304 as shown in FIG. 3B. Referring to FIG. 3C, a top down perspective reveals the sachet 100 conforming to the oven chamber 304 of the vaporizer device 302. Referring back to FIG. 3A, in particular embodiments, the user may seal the oven chamber 304 by inserting the top 306 over the oven chamber 304 by following path 310. As shown in FIGS. 3A-3C, the sachet 100 may be utilized in a plurality of different vaporizer devices 204, 302 because of the sachet's 100 ability to conform to the shape of an oven chamber of a vaporizer device.

In particular embodiments, during the vaporization process, the sachet 100 may be configured to allow heat transfer from a heating element of a vaporizer device to the herbal substance without comprising structural integrity of the sachet 100. The heat of the vaporizer device may vaporize the herbal substance 102 contained within the sachet 100 to release chemicals associated with the herbal substance 102. The perforations 106 of the sachet 100 allow for better heat transfer from the heating element of the vaporizer device to the herbal substance 102 of the sachet 100.

Figure 4:
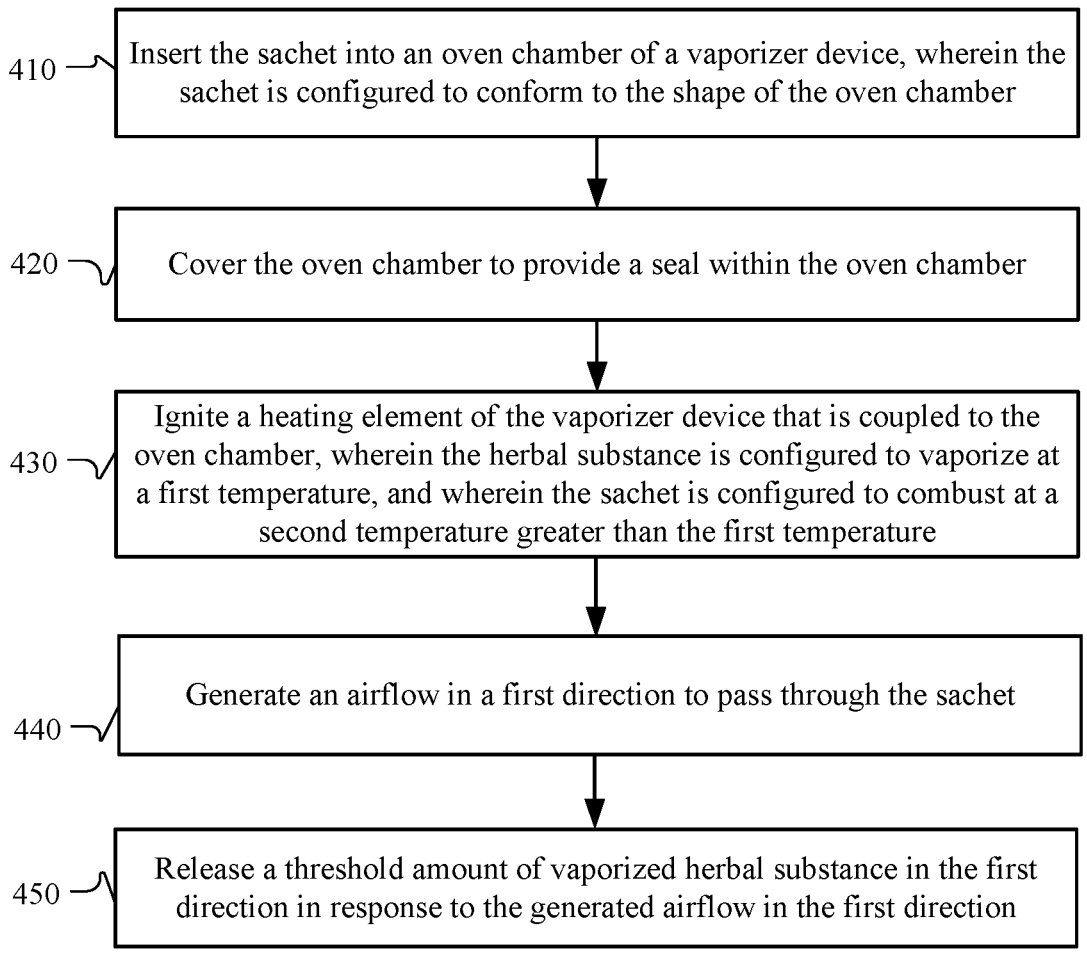
FIG. 4 illustrates an example method for vaporizing a sachet containing an herbal sub stance.

FIG. 4 illustrates an example method 400 for vaporizing a sachet containing an herbal substance. The method may begin at step 410, where a sachet may be inserted into an oven chamber of a vaporizer device. In particular embodiments, the sachet may be configured to conform to the shape of the oven chamber. At step 420, the oven chamber may be covered to provide a seal within the oven chamber. At step 430, a heating element of the vaporizer device that is coupled to the oven chamber may be ignited. In particular embodiments, the herbal substance may be configured to vaporize at a first temperature. In particular embodiments, the sachet may be configured to combust at a second temperature greater than the first temperature. At step 440, airflow may be generated in a first direction to pass through the sachet. At step 450, a threshold amount of vaporized herbal substance may be released in the first direction in response to the generated airflow in the first direction. Particular embodiments may repeat one or more steps of the method of FIG. 4, where appropriate. Although this disclosure describes and illustrates particular steps of the method of FIG. 4 as occurring in a particular order, this disclosure contemplates any suitable steps of the method of FIG. 4 occurring in any suitable order. Moreover, although this disclosure describes and illustrates an example method for vaporizing a sachet including the particular steps of the method of FIG. 4, this disclosure contemplates any suitable method for vaporizing a sachet including any suitable steps, which may include all, some, or none of the steps of the method of FIG. 4, where appropriate. Furthermore, although this disclosure describes and illustrates particular components, devices, or systems carrying out particular steps of the method of FIG. 4, this disclosure contemplates any suitable combination of any suitable components, devices, or systems carrying out any suitable steps of the method of FIG. 4.

Utilizing Sachet in other Contexts

In particular embodiments, the sachets 100 may be used in other contexts besides vaping. As an example and not by way of limitation, the user may heat/boil the sachets 100 within a container of water to release a threshold level of cannabinoids. For instance, the user may pour hot/boiling water in a cup with one or more sachets 100 to make a drink, such as a tea. As another example and not by way of limitation, the sachets 100 may be placed in a user's mouth similar to chewing or dipping tobacco. In particular embodiments, the sachets 100 may be customized accordingly to have specialized perforations 106 to allow transfer of the cannabinoids through the perforations 106 via the user's saliva.

Container for Sachets

In particular embodiments, the sachets 100 may be packaged by the manufacturing device into specific containers. As described above, the manufacturing device may package a threshold amount of sachets 100 together within a container. The container may be configured to hold the sachets 100 while maintaining moisture levels of the sachets 100. As an example and not by way of limitation, the container may comprise a humidifying element to maintain the moisture levels of the sachets 100. The herbal substance 102 contained within the sachets 100 may have an optimal vaporizing condition for a threshold period of time. The container may increase the threshold period of time of optimal vaporizing conditions by maintaining the moisture levels of the herbal substance 102 contained within the sachets. In particular embodiments, the container may be shaped to receive a plurality of sachets 100 and equally maintain the moisture levels of the sachets 100. As an example and not by way of limitation, the container may be shaped in as a cylindrical tin. As another example and not by way of limitation, the container may be shaped as a spherical container. In particular embodiments, the manufacturing device may be configured to customize the containers for certain brands. As an example and not by way of limitation, if a Company A would like to order a number of containers, the manufacturing device may be configured to brand the containers for Company A. The containers may be marked with a logo associated with Company A or the containers may be altered (e.g., shaped) to be made distinctly for Company A. In particular embodiments, the manufacturing device may be configured to brand the sachets 100 for certain brands. As an example and not by way of limitation, the manufacturing device may add company logos on each individual sachet 100. The manufacturing device may generate the sachets 100 in a size and shape specific for a particular company. The manufacturing device may use some kind of vaporizer safe substance to mark the sachets 100 with a brand. The manufacturing device may use a heating element to mark the sachets 100.

What is claimed is:

1. A sachet configured to contain an herbal substance, the sachet comprising:

a natural fiber layer of a first thickness that is configured to combust at a first temperature, wherein the natural fiber layer is shaped to contain the herbal substance, and wherein the herbal substance is configured to vaporize at a second temperature that is less than the first temperature; and a heat tolerant sealant configured to seal the natural fiber layer to contain the herbal substance, wherein the heat tolerant sealant is configured to deteriorate at a third temperature that is greater than the first temperature.

2. The sachet of claim 1, wherein the natural fiber layer comprises a cellulose layer within a range of porosity levels.

3. The sachet of claim 1, wherein the natural fiber layer comprises a plurality of layers.

4. The sachet of claim 1, wherein the heat tolerant sealant comprises a thermoplastic.

5. The sachet of claim 1, wherein the first thickness of the natural fiber layer is selected to have a threshold level of thermal conductivity.

6. The sachet of claim 1, further comprising a plurality of perforations within the natural fiber layer configured to provide heat transfer to the herbal substance.

7. The sachet of claim 1, wherein the sachet is configured to conform to shapes of a plurality of receptacles.

8. A sachet configured to contain an herbal substance, the sachet comprising:
- a natural fiber layer of a first thickness that is configured to combust at a first temperature, wherein the natural fiber layer is shaped to contain the herbal substance, and wherein the herbal substance is configured to vaporize at a second temperature that is less than the first temperature; and
- a thermoplastic layer of a second thickness coupled to the natural fiber layer, wherein the thermoplastic layer is configured to seal the natural fiber layer to contain the herbal substance, wherein the thermoplastic layer is configured to deteriorate at a third temperature that is greater than the first temperature.

9. The sachet of claim 8, wherein the natural fiber layer comprises a cellulose layer within a range of porosity levels.

10. The sachet of claim 8, wherein the natural fiber layer comprises a plurality of layers.

11. The sachet of claim 8, wherein the first thickness of the natural fiber layer is selected to have a threshold level of thermal conductivity.

12. The sachet of claim 8, further comprising a plurality of perforations within the natural fiber layer configured to provide heat transfer to the herbal substance.

13. The sachet of claim 8, wherein the sachet is configured to conform to shapes of a plurality of receptacles.

14. A method of vaporizing a sachet containing an herbal substance, the method comprising:
- inserting the sachet into an oven chamber of a vaporizer device, wherein the sachet is configured to conform to the shape of the oven chamber;
- covering the oven chamber to provide a seal within the oven chamber;
- igniting a heating element of the vaporizer device that is coupled to the oven chamber, wherein the herbal substance is configured to vaporize at a first temperature, and wherein the sachet is configured to combust at a second temperature greater than the first temperature;
- generating an airflow in a first direction to pass through the sachet; and
- releasing a threshold amount of vaporized herbal substance in the first direction in response to the generated airflow in the first direction.

* * * * *